United States Patent [19]

Coates

[11] Patent Number: 5,059,196
[45] Date of Patent: Oct. 22, 1991

[54] FEMORAL PROSTHESIS HOLDER/DRIVER TOOL AND METHOD OF IMPLANTATION USING SAME

[75] Inventor: Bradley J. Coates, Cordova, Tenn.

[73] Assignee: Dow Corning Wright Corporation, Arlington, Tenn.

[21] Appl. No.: 666,170

[22] Filed: Mar. 7, 1991

[51] Int. Cl.⁵ ............................................. A61B 17/56
[52] U.S. Cl. ................................... 606/99; 269/48.3; 269/229; 29/275
[58] Field of Search ..................... 606/99, 104; 623/20; 81/90.2, 113; 269/47, 48, 48.2, 48.3, 157, 217, 229; 29/275

[56] References Cited

U.S. PATENT DOCUMENTS

| D. 230,095 | 1/1974 | Rylee | D83/12 |
|---|---|---|---|
| D. 230,097 | 1/1974 | Rylee | D83/12 R |
| 1,893,414 | 1/1933 | Johnson et al. | 29/275 |
| 2,370,336 | 2/1945 | Wallace | 269/48.3 |
| 3,358,353 | 12/1967 | Banes et al. | 29/275 |
| 3,857,389 | 12/1974 | Amstutz | 128/92 EC |
| 4,642,121 | 2/1987 | Keller | 623/18 |
| 4,664,212 | 5/1987 | Nagatsuka et al. | 180/164 |
| 4,730,616 | 3/1988 | Frisbie et al. | 128/348.1 |

FOREIGN PATENT DOCUMENTS 619174  3/1949  United Kingdom ............... 269/48.3

OTHER PUBLICATIONS

"The Performance Knee" brochure, p. 16, published by Kirschner Med. Prods. (undated).

Custom Surgical Instruments, a division of La Ciudad Company, *Custom Surgical Instruments & Implants*.

*Primary Examiner*—Robert A. Hafer
*Assistant Examiner*—Kevin G. Rooney
*Attorney, Agent, or Firm*—John L. Chiatalas

[57] ABSTRACT

There is described a surgical tool and method for implanting a condylar prosthesis onto a femur using the tool. The prosthesis is of the type having a pair of posterior condyles which define an intercondylar notch opening including a distal internal contact surface extending anteriorly from the notch toward an anterior condylar flange. The tool comprises an elongated handle having a proximal end adapted for contact with the prosthesis and a distal end with an anvil for driving the prosthesis onto the distal aspect of the resected femur. One or more arms are attached to the proximal end of the shaft, including one or more anteriorly projecting fingers which are moved within the notch to engage the proximal internal contact surface. A pair of abutment pads are actuated to engage an external surface of the proximal condyle and exert a force opposite to the gripping finger(s) to securely lock and hold the prosthesis and tool together during implantation. The prosthesis is manipulated into position and seated on the resected bone while being driven at the anvil then, following implantation unlocked and the arms removed back from the notch to separate the tool from the implant. Alternatively, a pair of cooperating arms are pivotally attached to the proximal end of the shaft. The arms are separable from one another, once within the notch, and also include medial and lateral fingers, respectively, which engage a proximal internal retaining wall posteriorly of the notch.

13 Claims, 6 Drawing Sheets

FEMORAL PROSTHESIS HOLDER/DRIVER TOOL AND METHOD OF IMPLANTATION USING SAME

TECHNICAL FIELD

The invention relates generally to surgical instrumentation, particularly that used for the surgical implantation of femoral prostheses in the human knee.

BACKGROUND OF THE INVENTION

During the surgical implantation of femoral condylar prostheses, it is typically necessary to utilize some type of tool to hold and/or drive the prosthesis onto the distal aspect of a femur which has been resected and otherwise prepared to receive the implant. Currently, this procedure is accomplished by a variety of techniques, including the use of separate instruments for respectively holding and driving the prosthesis onto the bone. Alternatively, the same instrument has been used to both hold and drive the implant, but the aforementioned surgical approaches possess certain inherent disadvantages.

U.S. Pat. No. 3,857,389 to Amstutz describes a prosthesis holder having jaws which grasp the outer edges of a prosthetic member and are then locked in place, similar to a pair of Vise-Grip locking pliers, around the member. Similarly, the "Performance Knee", available through Kirschner Medical Products, Inc., utilizes a femoral driving instrument for impacting the prosthesis, driving it into place on a resected femur. The Kirschner instrument grips the prosthesis at notches formed along the lateral and medial edges of the condylar flanges, which is a disadvantage because the prosthesis is driven down onto the resected femur and disengaged, then another instrument is used to finish driving the prosthesis. This redundant procedural step inconveniences the surgeon and, moreover, such physical modifications to the prosthesis compromise the structural integrity of the resultant implant, and are therefore undesirable. Further, where the prosthesis is not modified as noted above, there is a further risk that the instrument jaws will impinge upon and further damage the soft tissue of the joint capsule exposed by the medical surgical incision.

Other instruments used in implanting prostheses are shown in U.S. Pat. No. Des. 230,097, disclosing a pusher used in total knee orthopedic procedures and U.S. Pat. No. 4,664,212, which shows an instrument for driving and removing a joint end of a prosthesis.

There yet remains a need for a combination holder/driver tool capable of securely gripping and positioning a femoral condylar prosthesis and driving it completely onto the resected distal femur of a patient during orthopedic surgery.

SUMMARY OF THE INVENTION AND ADVANTAGES

According to the invention, a surgical tool is provided for holding and driving an implantable condylar prosthesis onto a femoral bone. The prosthesis is of the type having an intercondylar notch opening defined between a pair of posterior condyles, including an internal distal contact surface extending anteriorly from the notch toward an anterior condylar flange. The tool comprises an elongated force-transmitting shaft having opposed ends, including a proximal end adapted for operative contact with the prosthesis and a distal end adapted for driving the shaft to implant the prosthesis onto the distal aspect of a resected femur. Means are located at the proximal end of the shaft for securely gripping the notch along the internal contact surface thereof and further means are provided for actuating the gripping means to releasably lock the tool and prosthesis together at the notch, allowing the prosthesis to be manipulated into position and seated in place by the tool while being driven from the distal end securely onto the femur, thereafter allowing the gripping means to be unlocked and disengaged from the notch when surgical implantation is substantially completed.

In a preferred embodiment, the gripping means of the invention comprises at least one arm having one anterior flange projecting within the intercondylar notch to grip the interior distal contact surface of the prosthesis.

In another preferred embodiment, the gripping means further comprises two arms having a lateral and a medial flange, respectively, which grip opposed lateral and medial contact surfaces of an internal distal retaining wall surrounding the intercondylar notch. The arms are separable from one another, causing the flanges to grip the internal distal retaining wall when the arms are inserted axially within the notch.

In still further aspects, there is provided a method of implantation using any of the holder/driver tools described above in conjunction with either the general or preferred embodiments of the invention.

An advantage of the instant invention is that no alteration need be made to the prosthesis to allow it to be gripped by the holder/driver tool.

Another advantage is that the holder/driver tool of the invention grips the prosthesis within the intercondylar notch, rather than along the lateral and medial edges of the distal condyles. Consequently, there is minimal risk of trauma to the underlying tissue of the joint capsule, from contact with various components of the tool.

A further advantage is that the tool of the instant invention grips what is a consistently-sized structure of typical femoral condylar implants, that is, the opening defined by the intercondylar notch, which does not require the medial-lateral adjustment necessitated by conventional tools having jaws that externally grip the condylar flanges and must allow for several size variations.

Yet a further advantage of the invention is that, by gripping and holding the prosthesis within intercondylar notch, a single instrument can be used to secure position, seat and then completely drive the prosthesis down onto the resected distal aspect of the femur. Thus, additional time-consuming steps, which are rather inefficient for the surgeon, are avoided using the procedure of this invention.

BRIEF DESCRIPTION OF THE DRAWINGS

The invention may be better appreciated by reference to the attached Drawings, which illustrate one or more preferred embodiments, wherein.

Further objects and advantages can be appreciated by reference to the ensuing Detailed Description, taken in conjunction with the above-mentioned Drawings, wherein the reference numerals are used to designate corresponding structures of the Drawings.

DETAILED DESCRIPTION OF ONE OR MORE PREFERRED EMBODIMENTS

Figure 1:
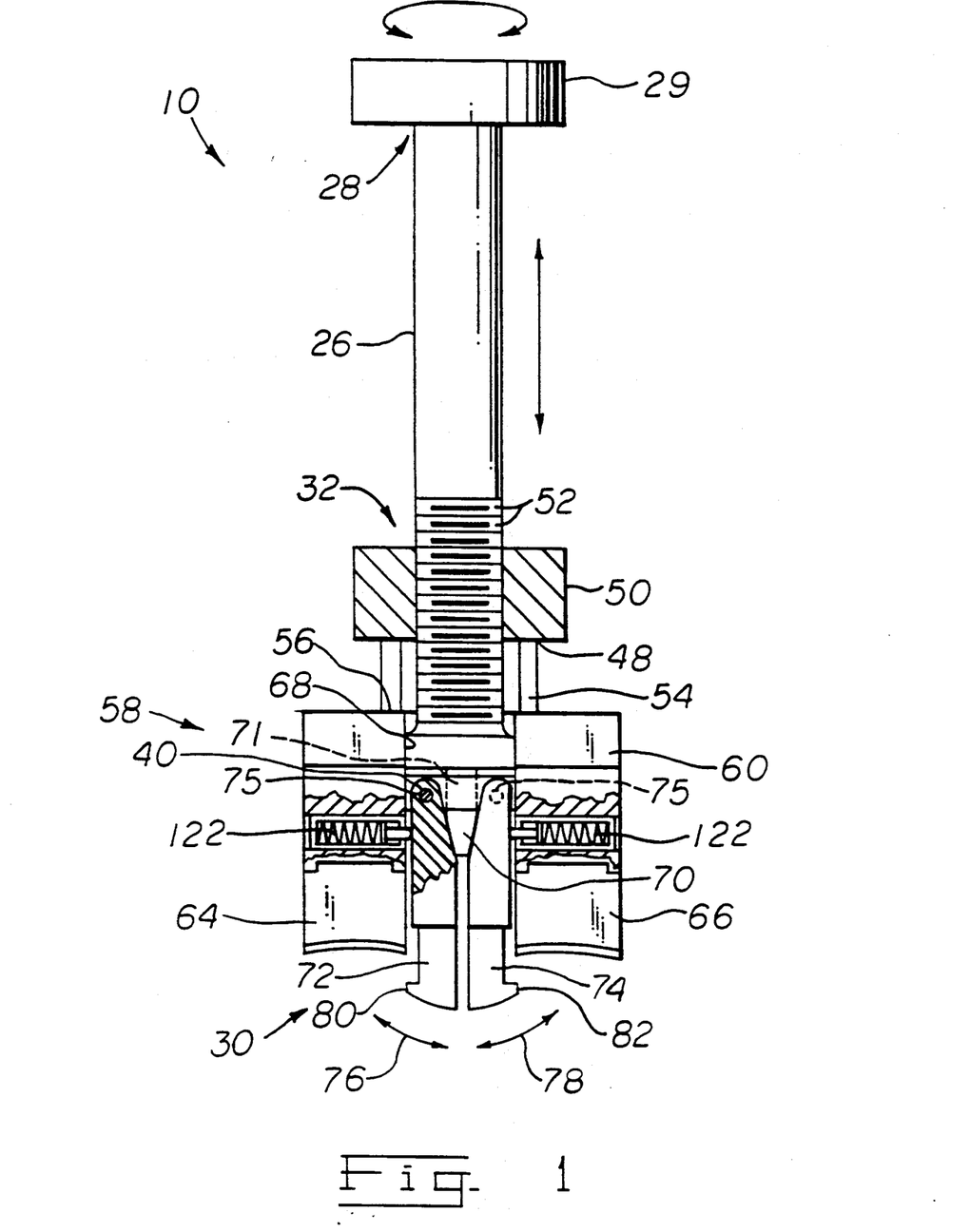
FIG. 1 is a side elevational view, partially cut-away, of the holder/driver of the invention.
Figure 5:
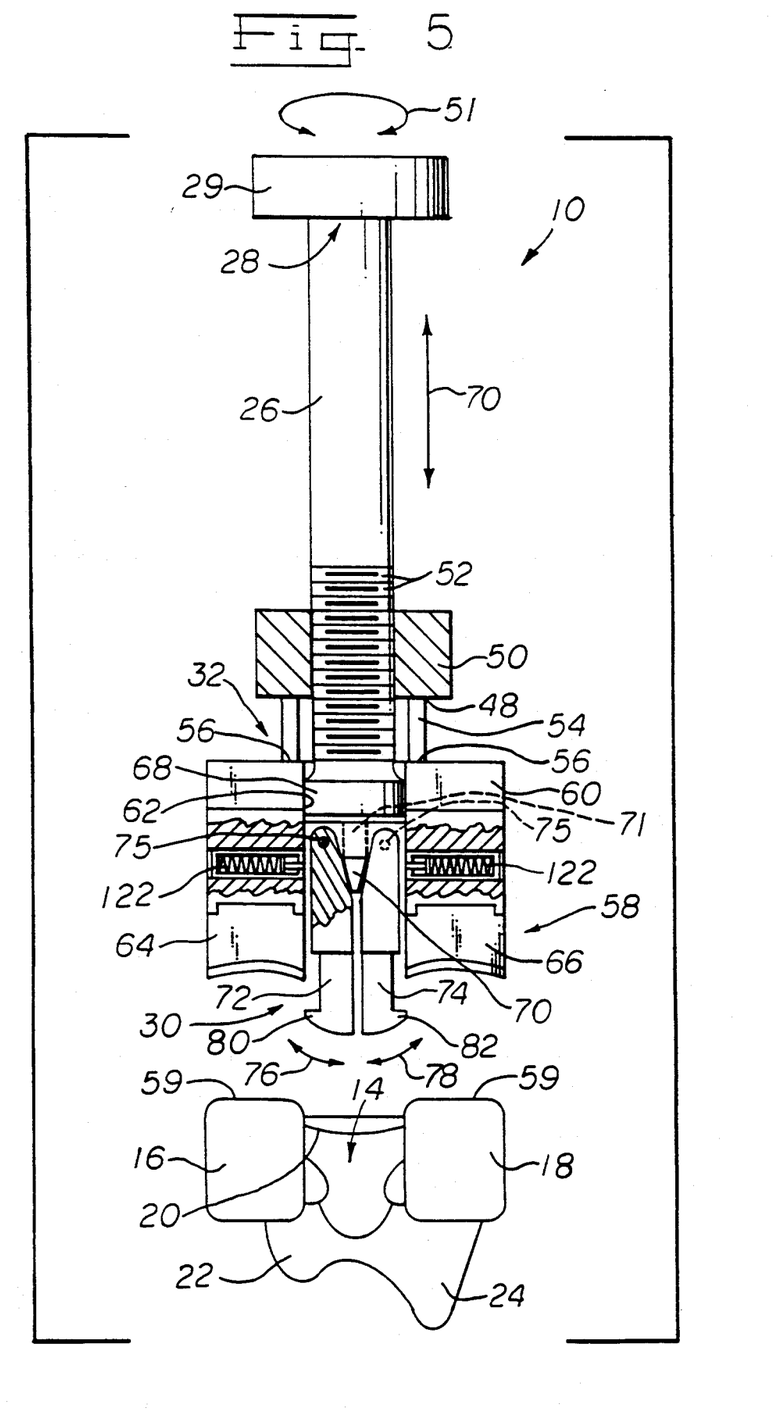
FIG. 5 is an overall view of the prosthesis/instrument combination, shown in the pre-assembled state, used to perform the surgical method of the invention.
Figures 6, 7:
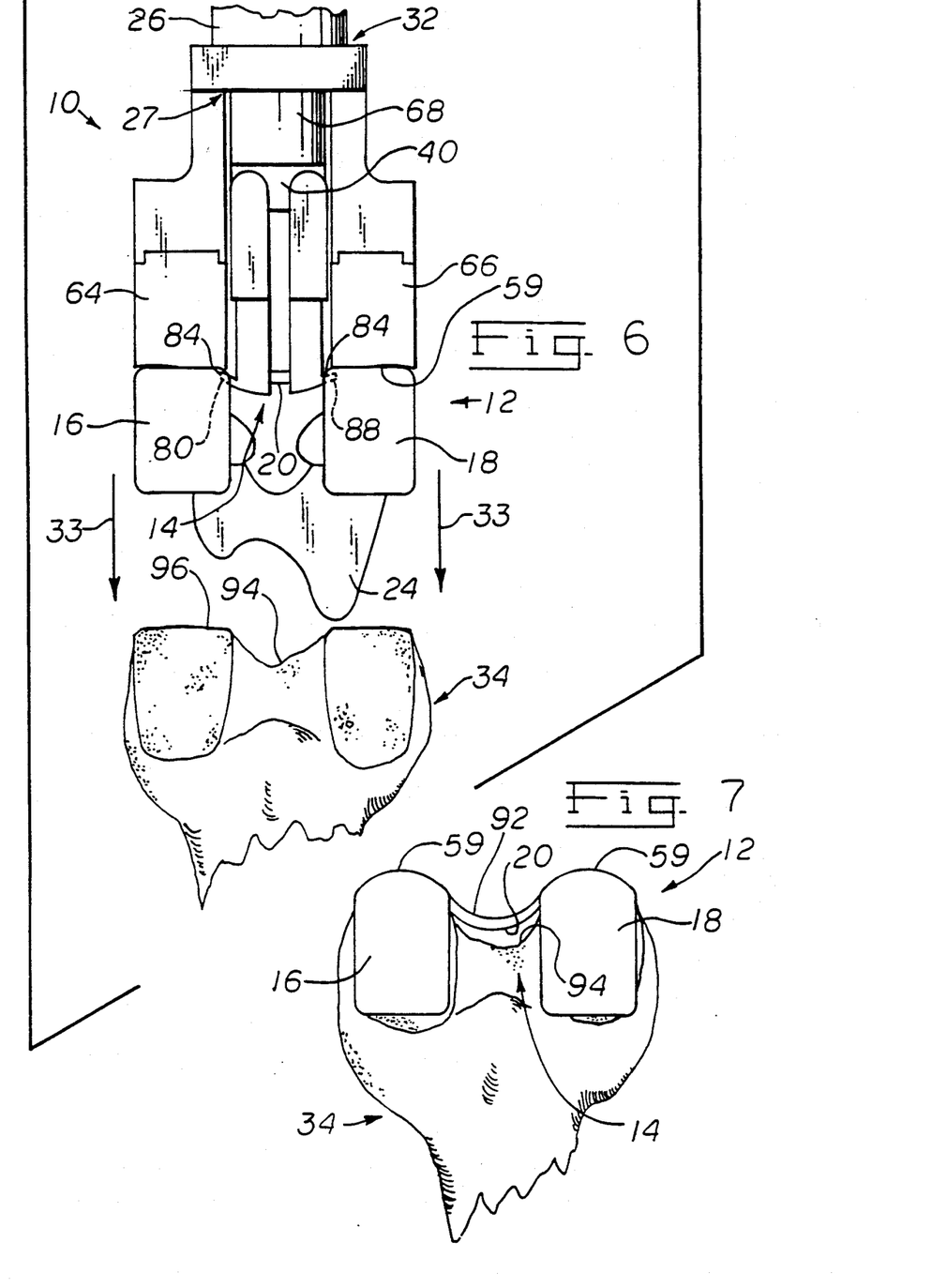
FIG. 6 is an overall view of the prosthesis/instrument combination, shown in an assembled state, being positioned on the resected bone, according to the surgical method of the invention.
FIG. 7 is an external perspective view, showing the implant finally installed on the distal aspect of the femur.

Referring to FIG. 1, there is generally shown a surgical tool 10 for holding and driving an implantable femoral prosthesis, generally shown at 12 (FIG. 7). With specific reference to FIGS. 5 and 7, the femoral prosthesis 12 is of the type generally having an intercondylar notch opening 14 defined between a pair of posterior condylar flanges 16, 18 and an internal contact surface 20 extending anteriorly from the notch toward an anterior condylar flange, consisting of medial 22 and lateral 24 portions, respectively. The tool 10 comprises an elongated force-transmitting shaft or handle 26 having a proximal portion 27, adapted for holding the prosthesis 12, and a distal portion 28 provided with an anvil 29 adapted for driving the shaft during implantation of the prosthesis.

Means generally shown at 30 are located on the proximal portion 27 of the shaft 26 for gripping the intercondylar notch 14 along the internal contact surface 20 of the prosthesis 12, which can then be manipulated by the surgeon using the handle 26 and securely positioned during implantation. The gripping means 30 is further depicted in combination with the prosthesis 12 by FIGS. 9-11.

Returning to FIGS. 1-2, and 5-6, means generally indicated at 32 are provided for actuating the gripping means 30 to releasably lock the tool 10 and prosthesis 12 together at the intercondylar notch 14, allowing precise manipulation of the prosthesis 12 downwardly (arrows 33) into alignment with the femur 34, (FIG. 6). A mallet is then used to strike the anvil 29 and drive the prosthesis 12 until it is implanted (FIG. 7). The actuating means 32 disengage the gripping means 30 to unlock the tool 10 from the prosthesis 12 when surgical implantation is substantially complete.

Figures 2, 3, 4:
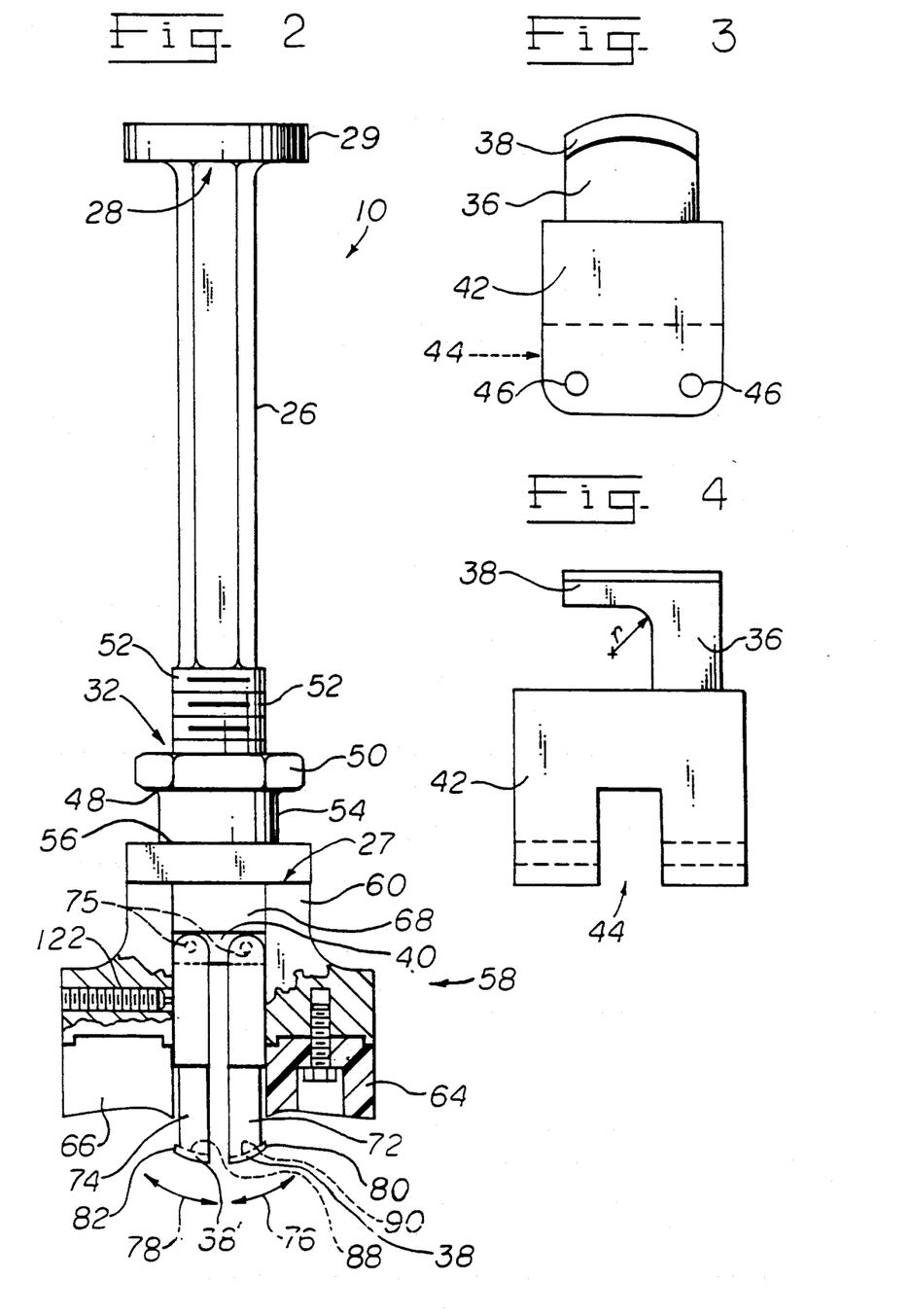
FIG. 2 is a side elevational view, partially cut away, showing an embodiment of the gripping means of the invention comprising a pair of separable arms.
FIG. 3 is an external frontal view of an alternative form of the gripping means of the invention, shown comprising a unitary arm.
FIG. 4 is an external side view of an alternative form of the gripping means shown in FIG. 3.
Figure 8:
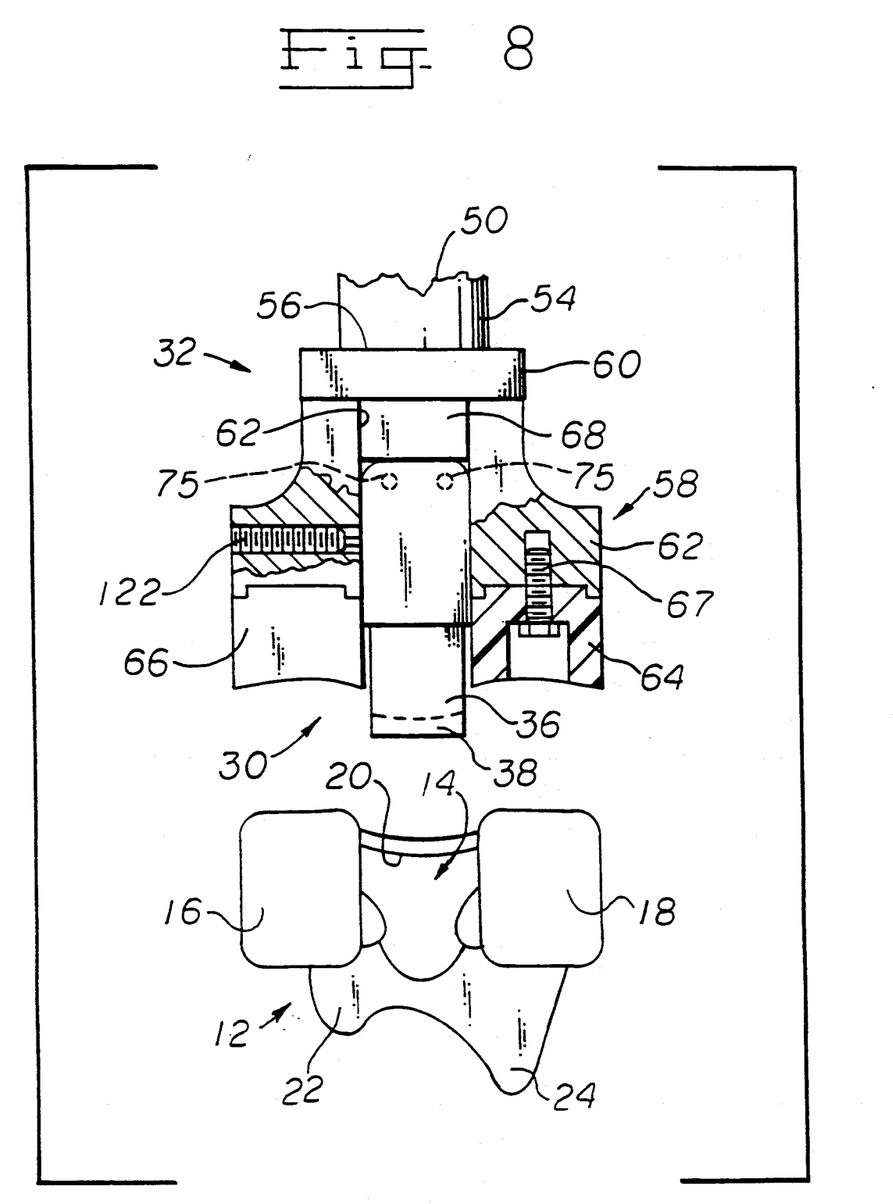
FIG. 8 is an enlarged overall view of the gripping means of the invention in combination with a prosthesis, shown in a preassembled state, with the gripping means comprising the unitary arm of FIGS. 3 and 4.

With reference to FIGS. 3, 4 and 8, the gripping means 30 preferably comprises a unitary arm 36 having an integral anteriorly gripping Finger 38 shown facing away from the viewer and projecting toward the internal distal contact surface 20. The width of the unitary arm 36, and particularly the anterior finger 38, is dimensioned to correspond to the width of the opening delimited by the notch 14, that is the arm 36 can be readily inserted into and withdrawn from within the intercondylar notch 14 together with the integral finger 38.

Figures 9, 10, 11:
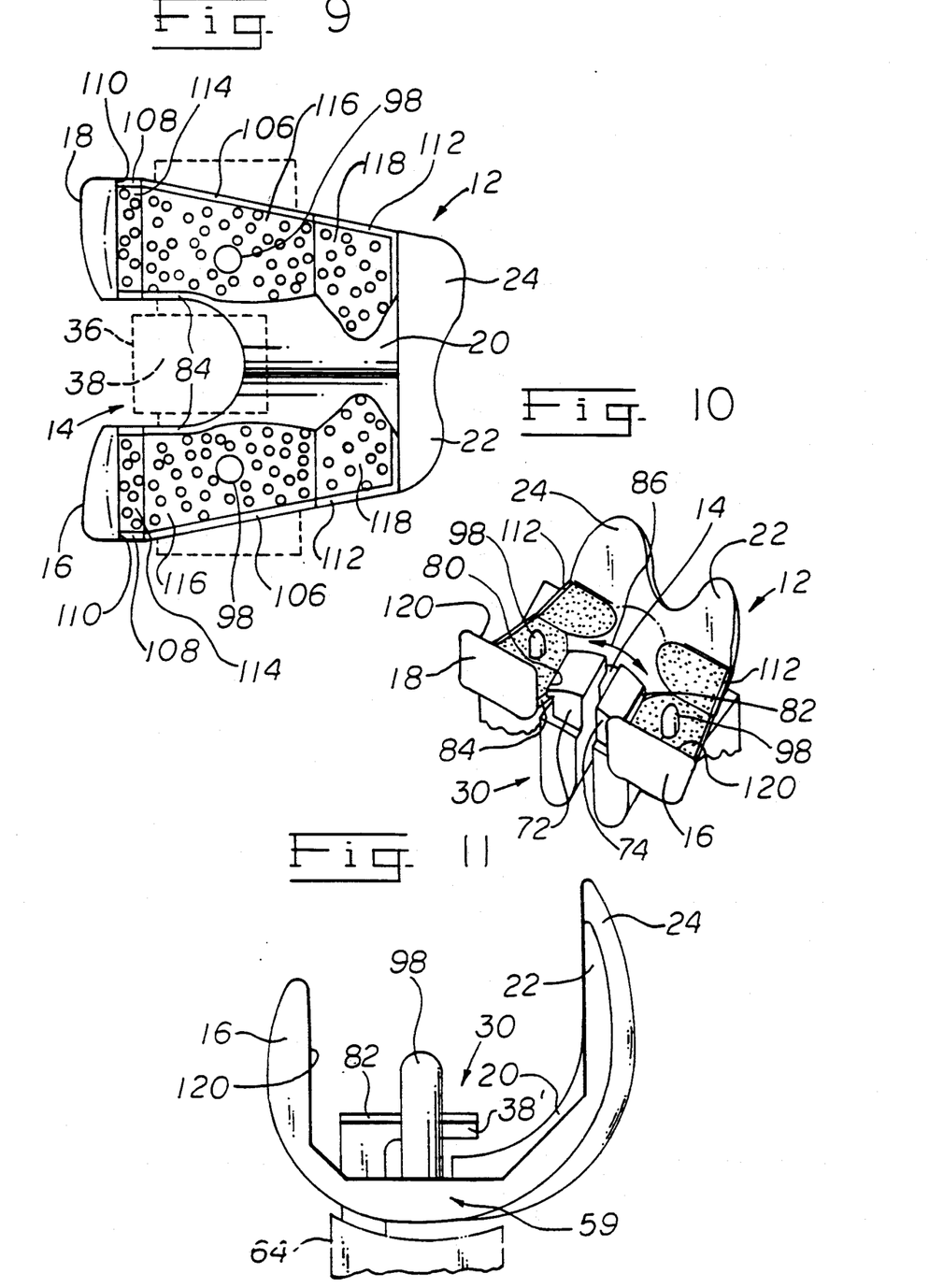
FIG. 9 is a top view of a prosthesis having particular use with the holder/driver of FIG. 8.
FIG. 10 is an external perspective view of the gripping means of the invention, shown comprising a pair of separable arms locked into place on a prosthesis prior to implantation.
FIG. 11 is a side view of the holder/driver and prosthesis combination shown in FIG. 10.

FIG. 9 shows the corresponding fit of the gripping means 30 within the notch 14, particularly the finger 38 of the arm 36 (shown in phantom); and FIGS. 3 and 4, further show the finger 38 adapted for gripping the distal internal contact surface 20 of the prosthesis 12, the finger 38 and arm 36 together preferably describing a radius r adapted to better conform to the curvature of the distal internal contact surface for improved gripping action. As further shown in FIGS. 3 and 4, the arm 36 has a base 42 provided with a slot 44 therein which receives a generally rectangular-shaped end 40 for mounting on the proximal portion 27 of the shaft 26, by means of pins 46.

Referring to FIGS. 1, 2, 5, 6, and 8, the actuating means 32 further comprises a jam nut 48, including a hexagonal head portion 50 tapped to engage the threads 52 extending along the distal end 27 of the shaft 26 and an elongated shank portion 54 terminating in a squared shoulder 56. The actuating means 32 cooperates with abutment means, generally indicated at 58, which engage external surface 59 of distal condyle on the prosthesis 12. Thus, the force exerted by the abutment means acts in direct opposition to the axial forces applied by the gripping means 30, as will be appreciated by those skilled in the art.

With reference to FIGS. 1, 2, 5 and 8, abutment means 58 further comprise a generally U-shaped support bracket 60 having an opening 62 through which the proximal portion 27 of the shaft 26 passes without threadedly engaging the opening 62 of the bracket 60. The proximal ends of the U-shaped extensions of bracket 60 are provided with mar-resistant pads 64, 66 affixed to the distal ends of bracket 60 by bolts 67 (FIGS. 2 and 8) or any suitable fastening means. The pads 64, 66 are preferably made from one or more of the following: polytetrafluoroethylene (PTFE), otherwise known as Teflon ®; ultrahigh molecular-weight polyethylene (UHMWPE); high durometer silicone; hard natural or synthetic rubber, or any other material capable of imparting an impact load without scratching or marring the highly polished articular surface of the metal prosthesis. The proximal end 27 of shaft 26 which projects through the aperture 62 of the bracket 60 (FIG. 1), terminates in a smooth cylindrical portion 68 (FIG. 2) having a diameter less than that of the aperture 62. As shown in FIG. 5, the proximal end 27 of shaft 26 freely slides through aperture 62 in the axial direction of arrow 70. Rotating jam nut 50 tightens the shank 54 against the top surface 56 of bracket 60, restricting axial movement arrow 70 of the shaft 26 relative to abutment means 58.

As shown in FIGS. 1, 2, 5, 10 and 11, gripping means 30 can alternatively comprise a pair of arms 72, 74 which each have anteriorly facing fingers 38', 38''; that grip the distal internal contact surface 20 of the prosthesis 12 (FIG. 5). The arms 72 and 74 are separable from one another, as shown by arrows 76, 78, and are caused to move apart either actively, through a spring-loaded mechanism assembly (not shown), or passively, via structure integral with the prosthesis (described below).

Arms 72, 74, have lateral 80 and medial 82 fingers, respectively, which are shown in further detail by FIGS. 6, 10 and 11, for gripping an internal distal retaining wall 84 surrounding notch 14.

FIGS. 9-10 depict the internal surface of prosthesis 12, particularly distal internal retaining wall 84. The retaining wall 84 is shown in FIG. 10 being gripped by the lateral 80 and medial 82 fingers. The combined lateral-medial width of arms 72, 74 is less than that of notch 14 when the arms are in a retracted conditions enabling the arms to be removed through the notch after implantation. As shown in FIG. 5, fingers 80, 82 are inserted within notch 14, their jam nut 50 is tightened-down, causing the fingers to spread apart (arrows 76, 78) and to grip distal internal retaining wall 84, (FIG. 6). Means, for spreading arms 72, 74 apart from one another extend across the distal internal contact surface 20, comprise a lateral-medial ridge or hump having a radius of curvature, indicated by arrow 86 in FIG. 10.

Referring to FIG. 2, anteriorly facing fingers 38' of arms 72, 74 have under surfaces 88, 90, respectively, which have a curvature complementary to that of the radius 86 (FIG. 10) to better grip distal internal contact surface 20. As the jam nut 50 is tightened to compress the anterior fingers 38' 38" against the ridged surface 20, the radius 86 causes arms 72, 74 to passively spread apart in the direction of arrows 76, 78 so that lateral 80 and medial 82 fingers engage and grip internal distal retaining wall 84 as impact pads 64, 66 exert an opposite pressure against the external surface of distal condyle 59. Referring to in FIG. 7, the ridged internal distal contact surface 20 of implant 12 is juxtaposed with patellar track 92 formed in the distal external surface 59, thus corresponding to the patellar groove 94 which naturally subsists in the resected distal surface 96 of the proximal femur 34. Moreover, a space 95 exists between the patellar groove 94 and surface 20, allowing the fingers 80, 82 (shown in phantom in FIG. 6) to be retracted from notch 14 when implantation is substantially complete.

As shown in FIGS. 9-11, the prosthesis 12 is provided with intergral pins 98 which are press-fit into corresponding holes milled in the resected surface 96 of the distal femur 34 during implantation in the direction of arrows 33 (FIG. 6).

The internal surface of the prosthesis 12 is shown in FIG. 9-11, further comprising distal retaining wall 106, posterior bevelled retaining wall 108, posterior retaining wall 110, anterior bevelled retaining wall 112, as well as internal distal retaining wall 84 described above. All of the retaining walls 84, 106, 108, 110 and 112 have smooth metal finishes and together define a plurality of planar areas comprising a beaded porous coating designed to allow bone tissue ingrowth into the implant for greater long-term stability. Specifically, the planar areas bounded by the retaining walls 106, 108, 110, 112 comprise posterior 114, distal 116 and anterior 118 porous surfaces, respectively. It should be noted that the distal internal contact surface 20, portions the internal surface 120 of the posterior condyles 16, 18 and the internal surface of the medial 22 and lateral 24 anterior condyle preferably comprise smooth, unbeaded surfaces minimizing frictional abrasion of the resected distal femur surface 96 as the implant is forced downwardly thereon in the direction of arrows 33 (FIG. 6).

Referring to FIGS. 1, 2, and 5, arms 72, 74 are pivotally attached to the base portion 68 located at the proximal end 40 of the shaft 26 by means of pins 75 (shown in phantom) which are press-fit and then welded to be hidden and present a smooth surface. In the embodiment shown in FIGS. 1 and 5, arms 72, 74 also are provided with slots (not shown) which extend perpendicularly of the pins 75, i.e., in the lateral-medial direction, and receive a complementary wedge portion 71 located at the distal end 40 of the shaft 26.

In operation, the distal surface 96 of the femur 34, shown for example in FIGS. 6 and 7, is initially prepared, using conventional tools and procedures well-known in the orthopedic surgery art, in order to receive the internal surface geometry of the implant 12. Surgical modification of patellar groove 94, for example, may be accomplished using the patellar track cutter guide disclosed in allowed United States Patent application Ser. No. 462,268, filed Jan. 9, 1990 of the present inventors, the entire disclosure of which is hereby incorporated by reference and relied upon. After the distal femur has been resected and otherwise prepared to receive the prosthesis 12, the tool 10 is affixed to the prosthesis in the above-described manner by loosing the jam nut 50 and distally moving the shaft 26 so that arms 72, 74, particularly anterior flange 38', lateral 24 and medial 22 fingers project between intercondylar notch 14. The jam nut 50 is then tightened down against the bracket 60, causing pads 64, 66 to engage external surface 59 of the distal condyle locking prosthesis 12 into place on the tool 10. The prosthesis 12 is then manually manipulated onto the resected surface 96 of distal femur 34 (arrows 33 in FIGS. 6). Once the prosthesis is seated to assure proper fit, the surgeon proceeds to securely mount the prosthesis onto the femur by applying force to the distal end of shaft 26 by striking the anvil 29 with a suitable mallet (not shown) or the like. Once the prosthesis 12 is substantially driven down onto the distal femur, as shown in FIG. 7, jam nut 50 is loosened and arms 72, 74 are forced back together by spring-loaded mechanism 122 (FIGS. 1 and 5) so that fingers 38; 80, 82 become disengaged and are withdrawn from notch 14.

With reference to the embodiment shown in FIGS. 3, 4, 8 and 9, the method of implantation is generally similar using the tool 10 with unitary arm 36 inserted within notch 14 (FIGS. 8 and 9) and anterior finger 38 gripping the distal internal contact surface 20 as jam nut 50 is tightened, causing the pads 64, 66 to abut external surface 59 of the distal condyle. Because no medial or lateral fingers are formed on arm 36, no gripping of internal distal retaining wall 84 occurs. For this purpose, the distal internal contact surface 20 can either be formed with a hump (not shown) or can be substantially planar depending upon the geometry of the finger 38 i.e., the finger 38 could have a radius (FIG. 3), as with gripping surfaces 88, 90 of flanges 38' (FIG. 2). Referring to FIG. 3, pins 46 which hold unitary arm 36 in place on proximal end 40 could be removable to allow a different geometry of the finger 38 to be substituted, depending on the structure of implant 12.

Obviously, many other modifications of the preferred embodiments could be made without departing from the scope and intent of the preceding disclosure, which is not intended to be construed as limiting in this regard.

That which is claimed is:

1. A surgical tool for holding and driving an implantable condylar prosthesis of the type having a pair of distal condyles which define an intercondylar notch opening, an anterior condylar flange and a distal internal contact surface extending anteriorly from the notch toward the anterior flange, the tool comprising:
  (a) an elongated force-transmitting shaft having opposed ends, including a proximal end adapted for operative contact with the prosthesis and a distal end adapted for driving the shaft to implant the prosthesis into the proximal aspect of a resected femur;
  (b) means located on the proximal end of the shaft for gripping the notch along the internal contact surface to securely hold the prosthesis during implantation; and
  (c) means for actuating the gripping means to releasably lock the gripping means within the notch, allowing the prosthesis to be manipulated into position on the femur while being driven from the distal end of the tool, and then allowing the tool to be disengaged from implant.

2. The tool of claim 1 wherein the gripping means further comprises an arm, including an anteriorly-projecting finger adapted to engage the proximal internal contact surface of the prosthesis.

3. The tool of claim 1 wherein the actuating means further comprises means for abutting an external surface of the proximal condyle to apply an axial force thereto which is in opposition to the axial force being exerted by the gripping means on the internal contact surface.

4. The tool of claim 3 wherein the actuating means further include means for proximally moving the gripping means from a retracted position to an advanced position within the intercondylar notch for engaging the proximal internal contact surface.

5. The tool of claim 4 wherein the abutment means further comprise a generally U-shaped bracket having a base with an opening through which the proximal end of the shaft passes, the actuating means further including a jam nut threadedly engaging the shaft distally of the bracket opening and tightening against a top surface of the bracket to adjustably move the gripping means relative to the abutment means and lock the tool and prosthesis together.

6. The tool of claim 2 further comprising a cooperating pair of arms having lateral and medial fingers adapted to engage an internal proximal retaining wall surrounding the intercondylar notch posteriorly of the internal distal contact surface, the arms being reversibly moveable toward one another a distance sufficient for passage within the intercondylar notch and away from one another sufficiently to allow the lateral and medial fingers to engage the internal distal retaining wall.

7. The tool of claim 6 wherein the movement of the cooperating arms toward one another is actuated by a spring-loaded mechanism.

8. A surgical tool for holding and driving an implantable condylar prosthesis of the type having a pair of posterior condyles which define an intercondylar notch opening, an anterior condylar flange and a proximal internal contact surface extending anteriorly from the notch toward the anterior flange and having a ridge that is contoured in a lateral-medial direction, the tool comprising:
  (a) an elongated force-transmitting shaft having opposed ends, including a proximal end adapted for operative contact with the prosthesis and a distal end adapted for driving the shaft to implant the prosthesis onto the distal aspect of a resected femur;
  (b) a pair of cooperating arms pivotally attached to the proximal end of the shaft, the arms including an anteriorly-projecting finger for gripping the prosthesis along the internal contact surface, and lateral and medial fingers, respectively, which are movable toward and away from one another and adapted to engage an internal proximal retaining wall surrounding the notch posteriorly of the proximal contact surface; and
  (c) actuating means for advancing the arms within and retracting them out from the notch, including abutment means for exerting on the external surfaces of the distal condyles a force in opposition to the force exerted by the anterior-projecting fingers, so that the lateral and medial fingers engage the proximal internal retaining wall and releasably lock the tool and prosthesis together, causing the arms to be moved apart by the ridge allowing the prosthesis to be manipulated into position on the femur while being driven from the distal end of the tool, then allowing the tool to be disengaged from the implant.

9. The tool of claim 8 wherein relative movement of the arm is assisted by a spring-loaded mechanism.

10. The tool of claim 9 wherein the shaft further comprises a handle for manipulation of the tool, including an anvil located at the distal end of the handle for driving the prosthesis onto the distal aspect of the femur.

11. The tool of claim 8 wherein the abutment means further comprises a nonmarring surface which contacts the external surface of the proximal condyle.

12. A method of implanting a condylar prosthesis onto the distal aspect of a resected femur, the method comprising the steps of:
  (a) providing the tool of claim 1 to grip the prosthesis;
  (b) affixing the prosthesis to the distal end of the tool;
  (c) holding and manipulating the prosthesis, using the shaft of the tool as a handle to seat the prosthesis on the resected femur;
  (d) applying force to the distal end of the shaft and driving the prosthesis onto the femur until the prosthesis is firmly attached; and
  (e) disengaging the gripping means from the proximal internal ridge and removing the gripping means from within the intercondylar notch.

13. A method of implanting a condylar prosthesis onto the distal aspect of a resected femur bone, the method comprising the steps of;
  (a) providing the tool of claim 8 to grip the prosthesis;
  (b) affixing the prosthesis to the proximal end of the tool;
  (c) holding and manipulating the prosthesis using the shaft of the tool as a handle, to seat the prosthesis on the distal aspect of the femur;
  (d) applying force to the distal end of the handle and driving the prosthesis onto the femur until the prosthesis is firmly attached; and
  (e) disengaging the gripping means from the proximal internal ridge and removing the gripping means from within the intercondylar notch.

* * * * *